United States Patent [19]

Braun

[11] Patent Number: 5,876,423
[45] Date of Patent: Mar. 2, 1999

[54] IMPLANTABLE STIMULATOR WITH TERMINAL VOLTAGE CONTROL OF A DEPLETABLE VOLTAGE SOURCE

[75] Inventor: Hans-Juergen Braun, Berlin, Germany

[73] Assignee: Biotronik Mess- und Therapiegeraete GmbH & Co. Ingenieurbuero Berlin, Berlin, Germany

[21] Appl. No.: 868,918

[22] Filed: Jun. 4, 1997

[30] Foreign Application Priority Data

Jun. 4, 1996 [DE] Germany ................... 196 23 788.2

[51] Int. Cl.$^6$ .......................................... A61N 1/37
[52] U.S. Cl. ................................................ 607/29
[58] Field of Search ........................ 607/12, 29

[56] References Cited

U.S. PATENT DOCUMENTS

| 3,707,974 | 1/1973 | Raddi . | |
|---|---|---|---|
| 4,345,603 | 8/1982 | Schulman | 607/29 |
| 4,448,197 | 5/1984 | Nappholz et al. . | |
| 4,548,209 | 10/1985 | Wielders et al. . | |
| 5,387,228 | 2/1995 | Shelton . | |

FOREIGN PATENT DOCUMENTS

| 0000983 | 3/1979 | European Pat. Off. . |
|---|---|---|
| 0431437 | 6/1991 | European Pat. Off. . |
| 0463410 | 1/1992 | European Pat. Off. . |

OTHER PUBLICATIONS

Greatbatch: "A New Pacemaking System Utilizing a Long–life Lithium Cell". In: Digest of the $9^{th}$ international conference on medical and biological Engineering, 1991, Melbourne, p. 27.

Primary Examiner—William E. Kamm
Attorney, Agent, or Firm—Venable; George H. Spencer; Robert Kinberg

[57] ABSTRACT

An implantable stimulator includes a depletable voltage source for supplying electrical energy. The voltage source has a terminal voltage which varies as a function of depletion of the voltage source. An output stage receives electrical energy from the voltage source and includes an arrangement for generating a stimulation voltage that is increased with respect to the terminal voltage of the voltage source and a stimulation energy storage device for storing the stimulation voltage. A control device receives operational energy from the voltage source and is operatively connected for controlling a stimulation operation of the stimulation energy storage device. A pump control device receives operational energy from the voltage source and is operatively connected to the output stage for controlling at least one of a time interval and a current strength of the electrical energy supplied to the output stage so that a minimum operating voltage required for a safe operation of the control devices is maintained as the terminal voltage of the voltage source.

12 Claims, 3 Drawing Sheets

IMPLANTABLE STIMULATOR WITH TERMINAL VOLTAGE CONTROL OF A DEPLETABLE VOLTAGE SOURCE

BACKGROUND OF THE INVENTION

The invention relates to an implantable stimulator including a depletable voltage source for supplying electrical energy, the voltage source having a terminal voltage which varies as a function of depletion of the voltage source; an output stage receiving electrical energy from the voltage source and including means for generating a stimulation voltage that is increased with respect to the terminal voltage of the voltage source and a stimulation energy storage device for storing the stimulation voltage; and a control device receiving operational energy from the voltage source and being operatively connected for controlling a stimulation operation of the stimulation energy storage device.

Implantable stimulators—among which heart pacemakers have attained the greatest importance, but among which implantable defibrillators as well as other muscle, nerve or bone stimulators for long term use also have been given increasing circulation have been increasingly developed in the past years, starting with the introduction of microprocessors at the end of the Seventies, into implements with a multitude of functions and extensive internal recognition and adaptation functions. Along with this went the increasing complexity and importance of their control for dependable functioning of the implements, so that the assurance of an uninterrupted supply of the digital control functions with sufficient operating voltage is a basic requirement for all such modern implements; see U.S. Pat. No. 4,448,197, for example, in this connection.

Such implements are usually battery-powered. Today, lithium batteries are practically exclusively employed as batteries, which provide a voltage of approximately 3 V, which is sufficient for the power supply of the control circuit(s) on the basis of integrated circuits—especially in CMOS technology—as well as for many stimulating tasks, and which have a large specific energy storage capability; see W. Greatbatch, "A New Pacemaking System Utilizing a Long-Life Lithium Cell"; Dig. 9th Intern. Conf. on Medical and Biological Eng., Melbourne, 1971.

However, like every electrochemical cell, lithium batteries also have a characteristic discharge curve, which is marked by a rise of the terminal resistance with increasing discharge, i.e. increasing length of use of the implanted implement. However, the maintenance of a dependable implement function requires the provision of stimulation pulses of a defined, constant voltage or those which, in many applications (for example with heart pacemakers) after a certain length of employment can be set even higher than the initial values. There are furthermore also applications—again especially with heart pacemakers, but particularly also with defibrillators or cardioverters—, in which the terminal voltage of even a fresh lithium battery is not sufficient for (dependably) meeting the stimulation task.

For these reasons heart pacemakers—as already proposed in the above mentioned publication of GREATBATCH and in more detail in U.S. Pat. No. 3,707,974—have output circuits with means for increasing (in particular multiplying) the output voltage in respect to the terminal voltage. In many cases these means are called "charge pump" or—after the main functional elements, namely switched capacitors—SC (switched capacitor) transformers, and usually include a so-called pump-capacitor, through which the energy is transferred from the battery into the output stage, and switching means for controlling the energy transfer assigned to it. An externally programmable charge pump operating on a digital basis with several pump capacitors and switches for realizing different output voltages is described in European Patent EP 0 000 983 B1. A modern arrangement of this type is described in U.S. Pat. No. 5,387,228, by means of which controlled or uncontrolled stimulation voltages can be made available as a function of the degree of battery exhaustion.

It is also known to equip heart pacemakers with means for indicating an extensive exhaustion of the battery—a so-called EOL (end-of-life) detection—, in order to assure the timely implantation of a fresh pacemaker before life-threatening losses of function occur.

An implantable stimulation device in accordance with the species is known from EP 0 463 410 B1, in which a lowest permissible value of the stimulation interval is preselected for a time dependent control of the pulse generator as a function of the degree of exhaustion of the battery.

The switch-over to a lower stimulation rate than that indicated by means of a physiological sensor, or from a mode of operation with high current use to one with lower current use when falling below a preselected battery voltage threshold, is proposed in EP 0 431 437 A2.

An implantable cardioverter is described in U.S. Pat. No. 4,548,209, wherein the time regime during the charge of the high voltage capacitor for making the cardioversion voltage (DC-DC conversion) available is controlled via an inductive coupling as a function of the voltage or the internal resistance of the battery.

With the known charge pumps the problem arises that their activation without paying attention to the degree of their exhaustion results in an uncontrolled drop of the terminal voltage, wherein there is a danger that this falls below the minimal voltage required for operating the control circuits. This can have very disadvantageous, possibly irreparable results for the function of the stimulator. The said problem can become relevant in actuality particularly, if it is necessary in the result of a stimulus threshold, to program an increased stimulation amplitude after an already extended length of operation of a pacemaker (i.e. with the battery already drained to a large extent).

SUMMARY OF THE INVENTION

It is therefore an object of the invention to provide an implantable stimulator of the species mentioned at the outset, in which a fall below the minimal voltage for operating the control circuit(s) because of the operation of the charge pump can be prevented to the greatest extent by means not affecting the pacemaker output.

The above and other objects are accomplished in the context of an implantable stimulator of the type first mentioned above, wherein according to the invention the stimulator additionally includes a pump control device receiving operational energy from the voltage source and being operatively connected to the output stage for controlling at least one of a time interval and a current strength of the electrical energy supplied to the output stage so that a minimum operating voltage required for a safe operation of the control devices is maintained as the terminal voltage of the voltage source.

This invention includes the concept of preventing an uncontrolled action of the charge pump even in case of a greatly exhausted battery and of operating the latter instead in such a way that in every case the uninterrupted maintenance of the minimum operational voltage for the control device of the implement is assured.

Advantageous further developments of the invention are featured in the dependent claims, or are explained in more detail below by means of the description of the preferred embodiment of the invention with reference to the drawings. Shown are in:

DETAILED DESCRIPTION OF THE DRAWINGS

Figure 1:
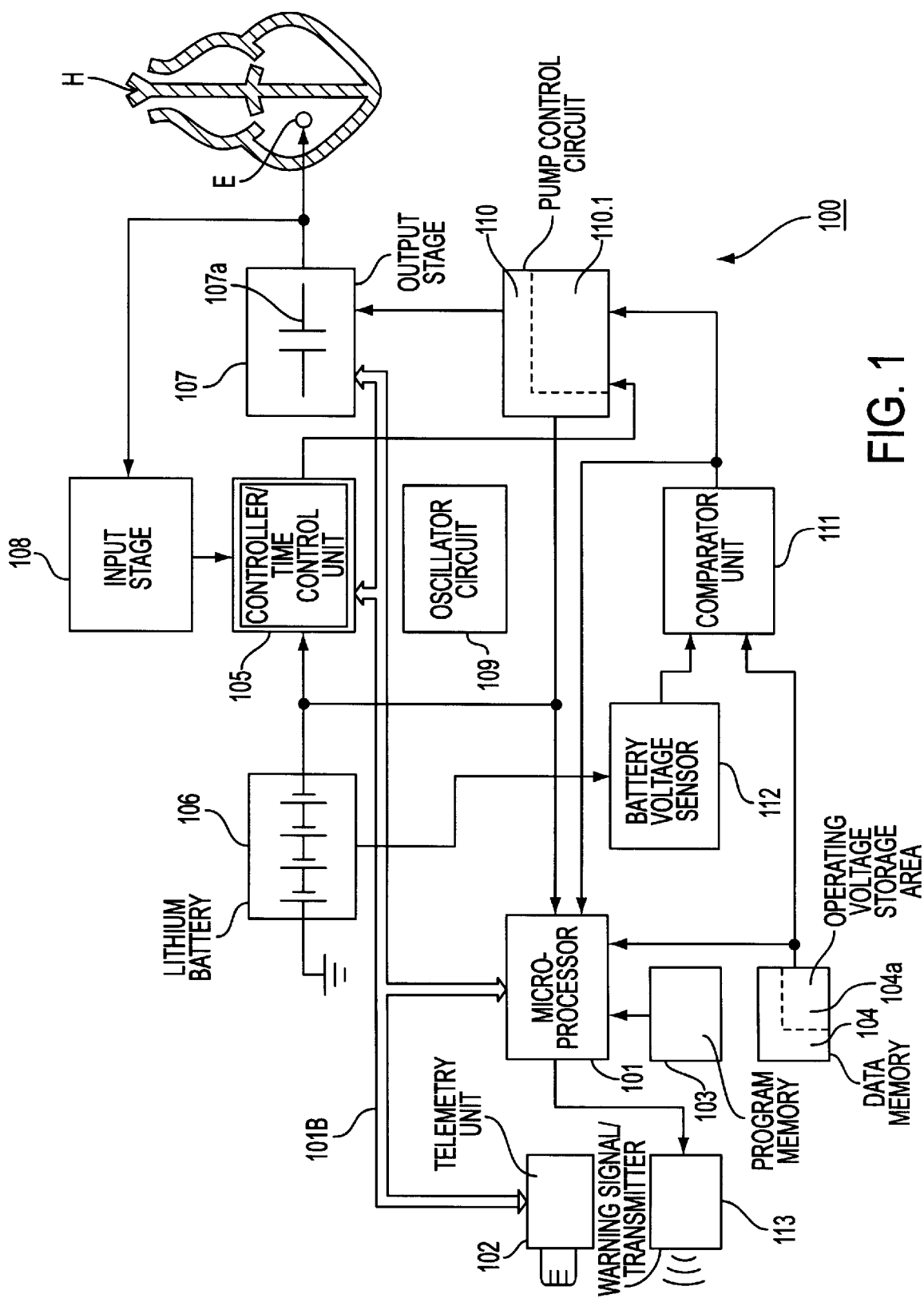
FIG. 1, a greatly simplified functional block diagram of the elements of a stimulator in accordance with one embodiment required for working the invention, FIG. 2, a functional block diagram of a modified embodiment, and FIG. 3, a representation of a detail of the arrangement in FIG. 2.

FIG. 1 schematically shows essential components of a one-chamber demand pacemaker 100, which is connected with the right heart chamber of a heart H, on the one hand for sensing the natural heart reactions and on the other for the demanded (intermittent) issue of stimulation pulses. A microprocessor 101, to which a telemetry unit 102 and a program memory 103 and a data memory 104 are assigned in the usual manner, as well as a controller/time control unit 105 are shown as the essential control component groups of the pacemaker 100.

It is symbolized by means of heavy lines that these control component groups are connected with a lithium battery 106 for power supply in the same way as (indirectly via a block detailed further down below) an output stage 107; all further current supply lines have been omitted for the sake of greater clarity of the representation. The output stage includes—symbolized by the capacitor identified by 107a—a storage capacitor arrangement for the storage of electrical energy for achieving a stimulation amplitude which is higher than the battery voltage.

A data and control signal bus 101B is represented as the means for the data and control signal exchange between the microprocessor 101, the telemetry unit 102, the controller/time control unit 105 and the output stage 107. An input stage 108 is connected in the customary way with the electrode E and is in a data signal connection with a control input of the controller/time control unit 105. An oscillator circuit 109 is furthermore associated with the input of the latter.

The controller/time control unit 105 is connected on the output side—besides the connections realized via the data bus 101B—by means of a control signal line with one of two control inputs of a pump control circuit 110, which in turn is looped into the current supply line between the battery 106 and the output stage 107. The pump control circuit 110 has a second control input, through which it is connected with the output of a comparator unit 111, whose one input is connected with a battery voltage sensor 112 and whose other input with an operating voltage storage area 104a of the data memory 104. The output of the comparator unit 111 is further connected with an input of the microprocessor 101, to which a warning signal transmitter 113 is assigned.

In this arrangement the stimulation pulse generation and output and most of the other operational sequences are controlled in a manner known per se, so that no special explanations are necessary in this respect.

First, the group of components formed by the battery voltage sensor 112, the operational voltage storage area 104a and the comparator unit 111 connected with the latter, for detecting the relation between the actual battery voltage and a stored minimum operational voltage of the microprocessor 101 and the controller/time control unit 105 (and possibly further component groups of the pacemaker), is essential in view of the execution of the invention. It is furthermore essential that the relation detected by means of the comparator unit 111 is used for controlling the energy transmission from the battery 106 to the output stage 107.

In the simplest case this takes place in such a way that, in case of a fall of the actual battery voltage below the minimum voltage, the signal issued by the comparator unit 111 to the pump control circuit 110 is applied as the trigger signal to the control input of a component (CMOS transistor, FET, or similar) or an appropriate circuit made of these. Following the issue of this control signal by the comparator unit 111, the maximum effective value of the pump current is therefore actively limited, i.e. reduced in comparison with the previously set, normally resistance-limited value. The load on the battery is reduced by this, so that the battery voltage will be slightly raised. As a result an average pump current will be set which is the maximum permissible for the actual battery exhaustion state.

Since in normal operation of a pacemaker the charge pump operates only during a portion of the length of time between the stimulation pulses, a reduction of the pump current can be compensated in a preferred way for the transport of a predetermined amount of charge into the output stage (within the limits set by the valid stimulation pulse interval); in this connection see further down. The programmed stimulation amplitude will therefore still be achieved for a defined remaining operating length of the pacemaker in spite of the pulse current limitation.

However, for safety's sake the output signal of the comparator unit 111, which causes a pump current limitation in the pump control circuit 110, is also simultaneously supplied to the microprocessor 101. The latter derives from this—possibly after additional correcting signal processing—a trigger signal for the warning signal transmitter 113, which (possibly by means of an acoustical signal, an additional electrical stimulating pulse or the like) signals to the patient the presence of a pump current limitation and therefore the need for an immediate consultation with the physician.

If the pump current limitation occurs as a result of the physician attempting to program an increased stimulation amplitude via the telemetry unit 102 in the course of a follow-up examination as a result of a stimulation threshold test, he is already informed immediately following the programming process of this result and, based on the warning signal—or on an additional response signal of the microprocessor 101 transmitted via the telemetry unit—he can stop the reprogramming and/or make a decision regarding the implantation of a fresh pacemaker.

In its execution the invention is not limited to the above recited preferred exemplary embodiment. Instead, a multitude of variants is conceivable, which make use of the represented solution also with different structures of the block circuit diagram and the employment of different components or groups of components.

Safety for the patient can be further increased, for example, in that in place of a single value of a minimal operational voltage, several safety voltage values, stepped in their amounts, are stored, and the comparator unit is embodied as a multi-stage threshold value discriminator, so that it outputs different output signals as a function of the fall below respectively one defined one of the stored operational voltage threshold values, a function which can be called a "tabulated EOL (end-of-life)".

Figure 2:
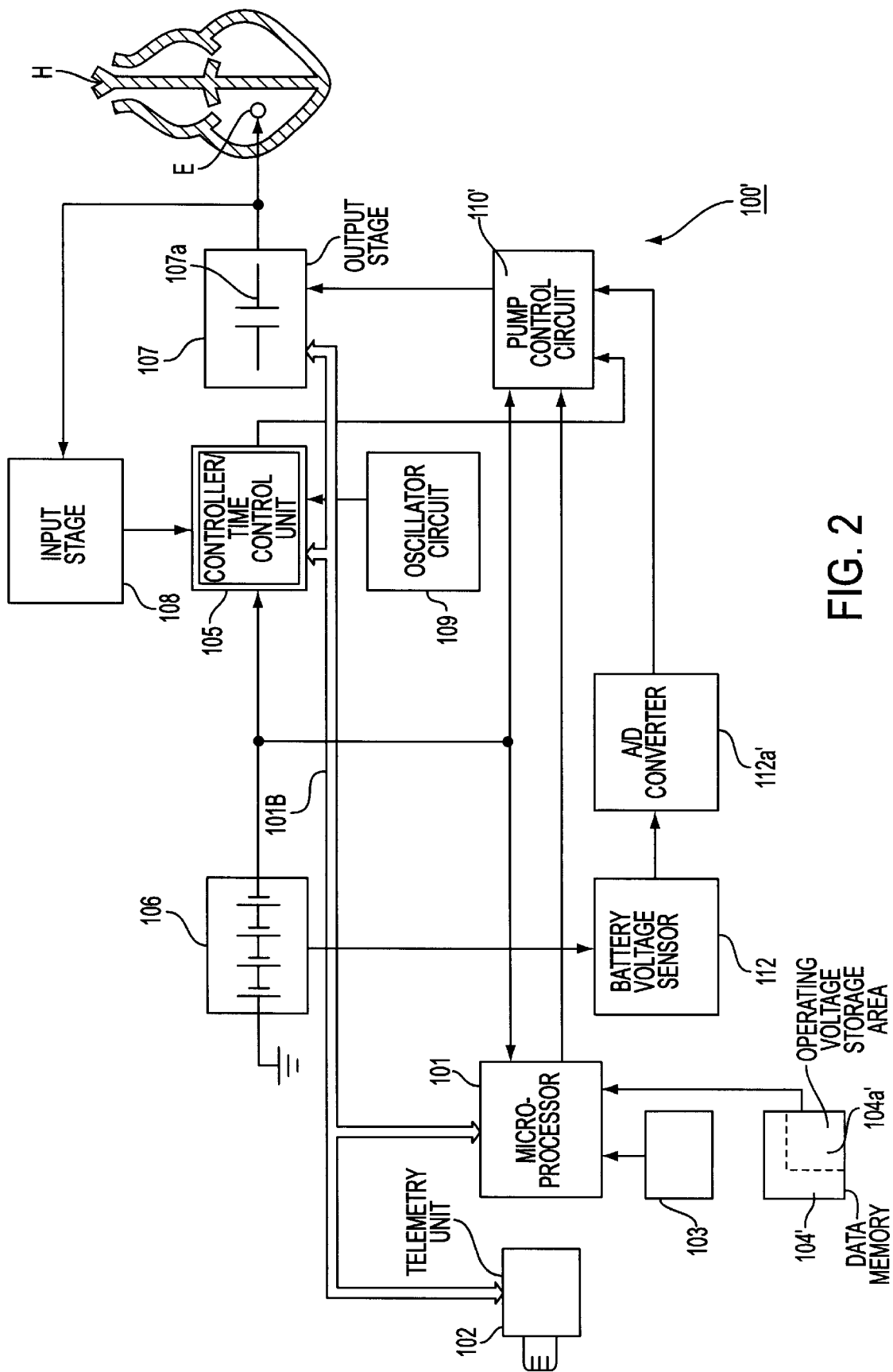

This function can also be realized with the modified embodiment of a pacemaker represented in FIG. 2. The pacemaker 100' in FIG. 2 differs from the embodiment described above by reference to FIG. 1 by an A/D converter 112a', connected downstream of the battery voltage sensor 112, and a considerably modified pump control circuit 110'. Otherwise, a warning signal transmitter has been omitted here and the memory 104 is therefore only connected with the microprocessor 101.

Figure 3:
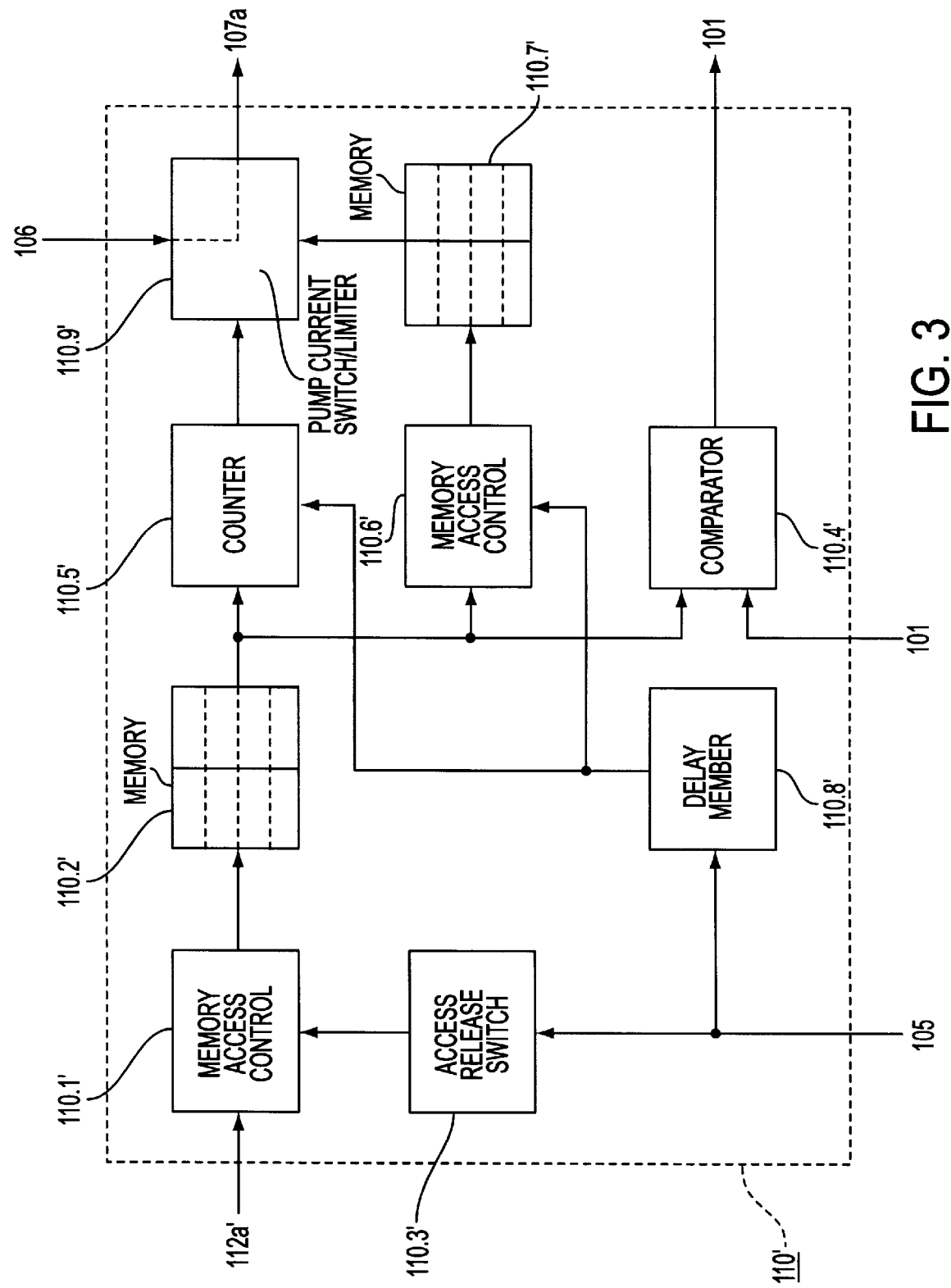

An advantageous embodiment of the pump control circuit 110' of FIG. 2 is sketched in FIG. 3. It accordingly comprises a memory access control 110.1' connected with the output of the A/D converter 112a' for addressing a memory area of a memory 110.2' constructed as a lookup table, in which predetermined pairs of values of battery voltage values and pump time interval values are stored for a value of the stimulation amplitude, in accordance with the actual battery voltage. The stored pairs of values have been preselected in such a way that increasing pump time intervals are assigned to decreasing battery voltage values by which, when applied, the battery load is successively reduced during the pumping process. The lowest voltage value of the table stored in the memory 110.2' corresponds to the minimum voltage for the operation of the pacemaker control stored in the memory 104a. In case of reprogramming of the stimulation energy it is necessary—depending on the size of the prestored data base—either to reprogram the memory 110.2' as a whole or to access another table of values (corresponding to the new value of the stimulation energy).

The memory access control receives a release signal from an access release switch 110.3', which is controlled via the controller 105 and permits a memory access in accordance with the actual battery voltage level respectively shortly after the issue of a stimulation pulse. The pump time interval value read out of the memory 110.2' is supplied as a count-setting value to a counter 110.5', as well as parallel therewith via a further memory access control 110.6' to a further memory 110.7', in which—again in tabulated form—values of a control variable of an active pump current limiter are stored in association with values of the pump time interval.

The clock input of the counter 110.5' is connected with the controller 105 via a delay member 110.8'. Following a delay in the delay member 110.8' sufficient for determining the pump time interval to be used, the counter 110.5' is started by the controller and counts clock pulses transmitted by the latter until the actually set pump time interval has been reached. When the counter starts, it releases a switch-on pulse to a pump current switch/limiter 110.9', which has been inserted between the battery 106 and the output capacitor 107a. At the same time the actual value of the control variable from the memory 110.7' is transmitted to it. Upon reaching the count value corresponding the set pump time interval, the counter 110.5' releases a signal, which blocks the pump current switch/limiter again and thus disconnects the battery from the output stage, through which the pump process is therefore terminated.

The pump time interval value read out of the memory 110.2' is also supplied to the one input of a comparator unit 110.4', to whose other input the actual value of the stimulation pulse interval transmitted by the microprocessor 101 is applied. If the pump time interval value which should be set in accordance with the battery voltage value is less than the actual stimulation interval, the function sketched above is directly executed.

But if the pump time interval is greater, i.e. if the exhaustion state of the battery has progressed so far that, because of the charge current limitation, the length of time of the stimulation interval is no longer sufficient for building up the required stimulation voltage at the output capacitor, the comparator unit sends an appropriate control signal to the microprocessor 101. Based on a prestored sequence, it is possible to react to this signal by extending the stimulation interval (reduction of the stimulation rate) and/or the deactivation of certain energy-intensive functions of the control device (for example the rate adaptation), i.e. by switching over to an emergency operating mode. In connection with this, the above mentioned function of the tabular EOL can be used, i.e. stepping of the safety amount portion of the stimulation energy. If the said situation occurs during reprogramming of the pacemaker, when the physician wants to increase the stimulation energy, the signal (transmitted in the usual manner via the telemetry) triggers a warning on the display of the programming device, upon the appearance of which the physician can think over the intended programming or can make a decision to replace the pacemaker.

Within the framework of possible modifications of the embodiment of the invention, the battery voltage sensor used in connection with the above examples can be replaced by a device for detecting the internal battery resistance by way of a current measurement. Furthermore, the detection of the actual battery state can be replaced by the detection and appropriate processing of data regarding the previous operational history. With such an embodiment, means for determining the effective elapsed operating time, means for storing of standard values of the battery state (for example the expected terminal voltage as a function of the effective operating length), as well as appropriate comparator means must be provided, whose output signal can take the place of a measured battery state value.

I claim:

1. An implantable stimulator, comprising:
   a depletable voltage source for supplying electrical energy, the voltage source having a terminal voltage which varies as a function of depletion of the voltage source;
   an output stage receiving electrical energy from the voltage source and including means for generating a stimulation voltage that is increased with respect to the terminal voltage of the voltage source and a stimulation energy storage device for storing the stimulation voltage;
   a control device receiving operational energy from the voltage source and being operatively connected for controlling a stimulation operation of the stimulation energy storage device; and
   a pump control device receiving operational energy from the voltage source and being operatively connected to the output stage for controlling at least one of a time interval and a current strength of the electrical energy supplied to the output stage so that a minimum operating voltage required for a safe operation of the control devices is maintained as the terminal voltage of the voltage source.

2. The implantable stimulator in accordance with claim 1, wherein the pump control device includes detection means for detecting the terminal voltage of the voltage source, and a controllable pump current limitation circuit having an input at least indirectly connected to an output of the detection means for limiting the current of the electrical energy supplied to the output stage during increasing depletion of the voltage source.

3. The implantable stimulator in accordance with claim 2, wherein the pump control device includes a pump time interval control device having an input at least indirectly connected to the output of the detection means for increasing the time interval together with the limiting of the current of the electrical energy supplied to the output stage during increasing depletion of the voltage source.

4. The implantable stimulator in accordance with claim 3, wherein the pump control device includes a first programmable, direct access memory for storing a plurality of values of the time interval, a first memory access control via which the first programmable, direct access memory is connected with an output of the detection means, a second programmable, direct access memory for storing values of a control variable of the pump current limitation circuit and having an output coupled to the pump current limitation circuit, and a second memory access control for addressing the second programmable, direct access memory.

5. The implantable stimulator in accordance with claim 3, wherein the pump time interval control device produces a stepped increase of the time interval within limits of a stimulation interval of the stimulator in response to a signal of the detection means indicating an increasing depletion of the voltage source.

6. The implantable stimulator in accordance with claim 2, wherein the pump control device includes a fixed value memory storing a minimal operating voltage and a comparator having a first input connected to an output of the detection means, a second input connected with the fixed value memory, and an output connected with a control input of the pump current limitation circuit.

7. The implantable stimulator in accordance with claim 6, wherein the detection means comprises a battery voltage sensor, the fixed value memory includes a plurality of stored stepped operating voltage threshold values, and the comparator comprises a multi-stage threshold value discriminator which releases different output signals as a function of a fall of a signal output from the battery voltage sensor below a respective one of the stored operating voltage threshold values.

8. The implantable stimulator in accordance with claim 6, further comprising a warning signal transmitter at least indirectly connected with an output of the detection means.

9. The implantable stimulator in accordance with claim 8, wherein the warning signal transmitter is connected to the output of the comparator via the control device.

10. The implantable stimulator in accordance with claim 2, wherein the pump current limitation circuit comprises a multi-stage peak current limiter for limiting a peak current supplied to the output stage.

11. The implantable stimulator in accordance with claim 1, wherein the implantable stimulator comprises a muscle or nerve stimulator which includes a bidirectional telemetry device for an external programing of the stimulation energy and for transmitting data indicating a depletion state of the voltage source.

12. The implantable stimulator in accordance with claim 11, wherein the implantable stimulator comprises a pacemaker.

* * * * *